United States Patent [19]

Shander et al.

[11] Patent Number: 5,132,293

[45] Date of Patent: Jul. 21, 1992

[54] ENZYMIC ALTERATION OF HAIR GROWTH

[76] Inventors: Douglas Shander, 16112 Howard Landing Dr., Gaithersburg, Md. 20878; F. Eugene Harrington, P.O. Box 200, 45 W. Main St., New Market, Md. 21774; Gurpreet S. Ahluwalia, 8632 Stable View Ct., Gaithersburg, Md. 20879

[21] Appl. No.: 784,650

[22] Filed: Oct. 28, 1991

Related U.S. Application Data

[63] Continuation of Ser. No. 567,018, Aug. 14, 1990, abandoned.

[51] Int. Cl.$^5$ .............. A61K 31/70; A61K 31/195; A61K 31/16; A61K 31/13
[52] U.S. Cl. ...................... 514/46; 514/564; 514/614; 514/671
[58] Field of Search .................. 514/46, 564, 614, 671

[56] References Cited

U.S. PATENT DOCUMENTS 4,720,489  1/1988  Shander ........................... 514/171
4,885,289  12/1989  Breuer et al. ..................... 514/170

FOREIGN PATENT DOCUMENTS 53-127432  11/1978  Japan .

OTHER PUBLICATIONS

Richards et al., "Expression of γ-Glutamyl Transpeptidase Activity in the Developing Mouse Tooth, Intervertebral Disc, and Hair Follicle", Cancer Research, 42:4143–4151 (1982).
Chase et al., "Critical Stages of Hair Development and Pigmentation in the Mouse", Physiological Zoology, 24:1–8 (1951).
De Young et al., "Localization and Significance of γ-Glutamyltranspeptidase in Normal and Neoplastic Mouse Skin", Cancer Research, 38:3697–3701 (1978).
Kinoshita et al., "The Synthesis of Antiglutin and Its Analogues", Bull. Chem. Soc. Jpn., 54:2219–2220 (1981).
Minato, "Isolation of Antiglutin, an Inhibitor of γ-Glytamyl Transpeptidase from *Penicillum oxalium*", Archives of Biochemistry and Biophysic, 192:235–240 (1979).
Porter, C. W. et al., Adv. Enz. Res., vol. 27:57–79 (1988).
Pegg, A. E., Cancer Res., vol. 48:759–74 (1988).
Pegg, A. E., The Physiology of Polyamines, vol. 1, Ch. 18, CRC Press, Boca Raton, Fla., pp. 303–314 (1988).
Heby, O., The Physiology of Polyamines, vol. 1, Ch. 5, CRC Press, Boca Raton, Fla., pp. 83–94 (1988).
Luk, G. D. et al., Am. J. Physiol., vol. 254:G194–G200 (1988).
Alhonen-Hongisto, L. et al., vol. 144(1):132–137, (1987), Biochem. Biophys. Res. Comm.
Casero, R. A. et al., Cancer Res., vol. 47:3964–67 (1987).
Henry, M. et al., Br. J. Derm., vol. 105:33–34 (1981).
Luk, G. D. et al., Cancer Res., vol. 42:3070–3073 (1982).
Rupniak, H. T. et al., Eur. J. Cancer Clin. Oncol., vol. 18:1353–9 (1982).
Peterson, L. L. et al., Biochim. Biophys. Acta, vol. 657:268–276 (1981).
Kanerva et al., (7/5/5), Arch. Toxicol., 59SUPPL(9):455, 1989.
Kousa et al., (7/5/24), Acta. Derm.-Venereol., 62(3):221–224, 1982.
McCullough et al., (7/5/9), J. Invest. Dermatol., 85(6):518–521, 1985.
McCullough et al., (7/5/16), J. Invest. Dermatol., 81(5):388–392, 1983.
Splinter et al., (7/5/8), Eur. J. Cancer Clin. Oncol., 22(1):61–67, 1986.

*Primary Examiner*—Frederick E. Waddell
*Assistant Examiner*—Diane Gardner
*Attorney, Agent, or Firm*—Fish & Richardson

[57] ABSTRACT

The rate and character of mammalian hair growth is altered by topical application to the skin of a composition containing a dermatologically acceptable carrier and an inhibitor of S-adenosylmethionine decarboxylase with or without an ornithine decarboxylase inhibitor.

10 Claims, No Drawings

ENZYMIC ALTERATION OF HAIR GROWTH

This is a continuation of application Ser. No. 07/567,018, filed Aug. 14, 1990, now abandoned.

This invention relates to alteration in the rate and character of mammalian hair growth by topical application through the skin of compositions containing an inhibitor of the enzyme S-adenosylmethionine decarboxylase.

BACKGROUND OF THE INVENTION

U.S. Pat. No. 4,039,669 describes the topical use of 17-alpha-R-androst-4-en-17-beta-ol- 3-one or esters thereof where the R is n-propyl or n-butyl for the control of dermatological systems associated with androgen-mediated conditions such as acne.

U.S. Pat. No. 4,139,638 and 4,161,540 describe the use of certain 4'-substituted and 3',4'-disubstituted anilides for the treatment of androgen-dependent disease states such as female hirsutism and acne.

U.S. Pat. No. 4,191,775 discloses that certain 3,4-disubstituted branched-chain fluorinated acylanilides may be used in the topical treatment of androgen-dependent disease conditions such as acne, female hirsutism, and seborrhea.

U.S. Pat. No. 4,344,941, describes the topical use of certain androgenic 17-alpha- substituted steroids exemplified by 17-beta- hydroxy-1-alpha-methyl-17-alpha(1-methyl-2- propenyl)-5-alpha-androstan-3-one for the treatment of diseases such as acne, seborrhea, alopecia and female hirsutism.

U.S. Pat. No. 4,367,227 describes a cosmetic composition for reducing sebum secretion from the skin comprising alcoholic solutions of cyproterone acetate.

West German OLS 2,840,144 describes the use of a combination of progesterone with either cyproterone acetate or chlormadinone acetate in the topical treatment of androgen induced hormonal disturbances such as alopecia, female hirsutism, and acne.

Japanese Kokai 58-57308 describes the restoration of hair to bald heads by the topical applications of oxidizing substances such as stabilized chlorine dioxide, potassium bromate, or ozone to suppress the enzymatic activity of the reductive enzyme 5-alpha-reductase.

The patent art discloses a number of ways of reducing the growth of human hair as opposed to its conventional removal by cutting, shaving, or depilation. One such method is described in U.S. Pat. No. 3,426,137, which pertains to a process for inhibiting the growth of hair by the topical application to a depilated skin area of a composition containing a substituted benzophenone such as 2-amino-5-chloro-benzophenone. Examples in the patent illustrate the reduction of hair growth on the back area of rabbits and on the arm of a male human subject.

Another process for extending the duration of depilation is described in U.S. Pat. No. 4,370,315. The process therein comprises the topical application of a composition containing a lipoxygenase along with linoleic acid or derivative thereof. The patent describes the application of such composition to various body parts of female human subjects in the majority of which regrowth of hair was clearly perceptible only after six or more weeks.

In U.S. Pat. No. 4,439,432 topical compositions containing progesterone are reported for use in treatment of progesterone deficiency and related conditions, including abnormal hair growth resulting from androgen excess. Further insights on this point may be obtained from the related literature, among which mention may be made of Simpson et al. "The Effect of Topically Applied Progesterone on Sebum Excretion Rate,") Br. J. Derm., Vol. 100, p. 687 (1979), in which progesterone was reported effective in reducing sebum excretion rates in females, but without effect in males. In Goos et al., "An Improved Method for Evaluating Antiandrogens," Arch. Dermatol. Res. Vol. 273, pp. 333-341 (1982), the effect of progesterone on inhibition of hair growth in intact males appears to be doubtful (p. 340, Table 3, Group VI vs. Group X). In Burdick et al., "The Topical Effect of the Antiandrogen Chlormadinone Acetate and Some of Its Chemical Modifications on the Hamster Costovertebral Organ," Br. J. Derm., Vol. 82, Supplement 6, p.19 (1970), antiandrogens were either ineffective or of questionable effect in inhibiting flank organ function in normal intact male hamsters. Similarly, in Girard et al., "Inhibition of Testosterone Metabolism and Lipogenesis in Animal Sebaceous Glands by Progesterone," Arch. Dermatol. Res., Vol. 269, pp. 281-290 (1980), progesterone is found effective in the female but not in the male. In all of the above experiments topical antiandrogens were ineffective in males in inhibiting androgenic function. When the female and male responses were compared in both humans and hamsters, only females responded to topical treatment.

In U.S. Pat. No. 4,269,831 a substantial reduction in hair growth of the hamster flank organ is among the effects reported from topical application of $17\beta$-hydroxy-$17\alpha$-propylandrost-4-en-3-one. However reduction in the size of the flank organ is also described, leaving a smaller field on which the hair can grow. Therefore, the reduction in hair growth may be a consequence of a decrease in area of the flank organ rather than an alteration in the character of the hair.

U.S. Pat. No. 4,885,289 describes altering the rate and character hair growth by topical application of 5-alpha-reductase inhibitors and/or cytoplasmic androgen receptor binding agents, while U.S. Pat. No. 4,720,489 describes the topical application of ornithine decarboxylase inhibitors for similar purposes, either alone or in combination with the materials of U.S. Pat. No. 4,885,289.

Although it has been theorized that a variety of enzymes are involved in the growth of the cells of human hair, the relationship between such enzymes and between the reactions which they control, as well as their effect upon each other has not been fully understood, as appears from Pegg, Cancer Research, Vol. 48, 759-774 (1988); Gupta et al., Molec. and Biochem. Parasitology, Vol. 23, 247-252 (1987); and Elo et al., Cancer Letters, Vol. 41, 21-30 (1988).

It has now been found that the rate and character of mammalian (including human) hair growth can be altered by topical application to the skin of a composition containing an inhibitor of S-adenosylmethionine decarboxylase (SAMDC), and further that such an inhibitor can be applied in combination with an ornithine decarboxylase inhibitor to produce greater effects than either inhibitor alone. Compositions containing one or a combination of both inhibitors in any conventional nontoxic dermatologically acceptable carrier or vehicle can be used for application of the combination to the desired areas of the skin. Such compositions may contain 0.1 to 50%, based on the total weight, of an inhibitor of SAMDC, and from 0.1 to 20% of an ornithine decarboxylase inhibitor.

Among the known inhibitors of SAMDC are methylglyoxal bis(guanylhydrazone) (MGBG); diethylglyoxal bis(guanylhydrazone) (DEGBG); and 5'-deoxy-5'-[N-methyl-N-(2-[aminooxy]ethyl)] aminoadenosine (MAOEA).

Among the known ornithine decarboxylase (ODC) inhibitors which can be used are those described in U.S. Pat. Nos. 4,201,788; 4,413,141, 4,421,768; and 4,720,489; of these, the preferred ODC inhibitors are 2-(difluoromethyl)-ornithine(DFMO); alpha-ethynyl ornithine; 6-heptyne-2,5-diamine, and 2-methyl-6-heptyne-2,5-diamine. In choosing ODC inhibitors for use in the practice of this invention, it is important to avoid those known to have secondary pharmacological effects such as 5-hexyne-1,4-diamine, which is known to bring about increases in brain 4-aminobutyric acid levels by a transformation catalyzed by mitochondrial monoamine oxidase. To minimize the risk of alteration of other bodily functions through systemic action, it is preferred to apply the ODC inhibitors in compositions such that the level of application will range from about 1 to about 2000 micrograms of active material per square centimeter of skin; still more preferred is the application of about 50 to about 500 micrograms per square centimeter of skin.

The SAMDC inhibitor or inhibitors is also preferably applied so that the amount of active material is from about to about 5000 micrograms per square centimeter of skin.

The relative proportions of SAMDC inhibitor and of ODC inhibitor in the compositions as applied to the skin is not critical and may be varied over a wide range; preferred are compositions in which the relative proportions range from 1:0 to 10:1 by weight.

The following specific examples are intended to illustrate the nature of the invention without acting as a limitation on its scope.

EXAMPLE 1

A vehicle or carrier was prepared having the following composition:

| Component | Wt. Percent Concentration |
|---|---|
| Water | 68% |
| Ethanol | 16% |
| Propylene Glycol | 5% |
| Dipropylene Glycol | 5% |
| Benzyl Alcohol | 4% |
| Propylene Carbonate | 2% |

A series of compositions was prepared each containing a given concentration of specified inhibitor in the foregoing vehicle, as listed in Table 1 below.

Four groups (eight animals in each group) of male intact Golden Syrian hamsters were provided. These animals were considered acceptable models for human beard hair growth in that they display oval shaped flank organs, one on each side, each about 8 mm in major diameter, which grow thick black and coarse hair similar to human beard hair. These organs produce hair in response to androgens in the hamster. The flank organs of each hamster were depilated by applying a thioglycolate-based chemical depilatory (Surgex), and to one organ of each animal was applied 10 μL. of vehicle alone once a day, while to the other organ of each animal was applied an equal amount of vehicle containing inhibitor. After 14 such applications (Mon.-Fri.) over a period of 18 days, the flank organs were shaved and the amount of recovered hair (hair mass) from each was weighed. The extent of reduction in hair growth by the inhibitor was expressed as the percent decrease in hair mass on the organ treated with inhibitor as compared to the organ treated with vehicle alone. As a control, one group of eight animals had both flank organs of each animal treated with vehicle alone. The results were as shown in Table 1 below.

TABLE 1

| | Flank Organ Hair Mass | | |
|---|---|---|---|
| | (mg ± SE) | | Hair Growth |
| Inhibitor | Treated | Control | Inhibition (%) |
| 5% MAOEA | 2.03 ± .18 | 2.68 ± .13 | 29.4 ± 5.9 |
| 5% MGBG | 1.54 ± .22 | 2.63.22 | 40.3 ± 7.4 |
| 5% DFMO | 0.99 ± .08 | 2.89 ± .22 | 64.3 ± 3.7 |
| 5% MAOEA and 5% DFMO | 0.76 ± .11 | 2.66 ± .18 | 70.9 ± 4.8 |
| None | 3.04 ± .24 | 3.05 ± .20 | 0 ± .53 |

EXAMPLE 2

The same procedure was followed as in Example 1 except that the vehicle used for the compositions consisted of water alone. The compositions used and the results obtained were as shown in Table 2 below:

TABLE 2

| | Flank Organ Hair Mass | | |
|---|---|---|---|
| | (mg ± SE) | | Hair Growth |
| Inhibitor | Treated | Control | Inhibition (%) |
| 2.5% DEGBG | 2.62 ± .15 | 3.15 ± .17 | 15.9 ± 5.2 |
| 5% DFMO | 2.70 ± .22 | 3.37 ± .22 | 18.8 ± 3.7 |
| 2.5% DEGBG and 5% DFMO | 2.30 ± .26 | 2.91 ± .21 | 21.7 ± 5.3 |

EXAMPLE 3

Compositions were prepared as described in Example 1 containing the inhibitors listed in Table 3. The same test procedure was followed except that the compositions were applied to the hamster flank organs every day for fifteen successive days, at which time hair mass was measured; the results were as follows:

TABLE 3

| | | Flank Organ Hair Mass | | |
|---|---|---|---|---|
| | No | (mg ± SE) | | Hair Growth |
| Inhibitor | Animals | Treated | Control | Inhibition (%) |
| 5% MGBG | 6 | 0.56 ± .11 | 0.99 ± .13 | 42.3 ± 8.2 |
| 5% DFMO | 7 | 0.49 ± .14 | 0.92 ± .13 | 44.4 ± 18.2 |
| 5% MGBG and 5% DFMO | 8 | 0.16 ± .03 | 0.87 ± .08 | 80.7 ± 3.2 |
| None | 7 | 0.85 ± .13 | 0.91 ± .21 | 6.47 ± 10.0 |

Similar results can be obtained with other inhibitors of SAMDA and of ODC.

What is claimed is:

1. The process of reducing the rate and altering the character of mammalian hair growth which comprises the step of applying to the skin a composition containing an inhibitor of S-adenosylmethionine decarboxylase, the amount of said inhibitor per unit area of skin being effective to reduce the rate and alter the character of said hair growth.

2. The process as claimed in claim 1 in which said composition contains in addition an ornithine decarboxylase inhibitor.

3. The process as claimed in claim 1 or 2 in which said inhibitor of S-adenosylmethionine decarboxylase is selected from the group consisting of methylglyoxal bis (guanylhydrazone), diethylglyoxal bis (guanylhydrazone), and 5'-deoxy-5'-{N-methyl-N-}aminodenosine.

4. The process as claimed in claim 2 in which said ornithine decarboxylase inhibitor is selected from the group consisting of 2-(difluoromethyl)-ornithing, alpha-ethynyl ornithine; 6-heptyne-2,5-diamine and 2-methyl-6-heptyne-2,5-diamine.

5. The process as claimed in claim 4 in which said inhibitor of S-adenosylmethylthionine decarboxylase is selected from the group consisting of methylglyoxal bis(guanylhydrazone), diethylglyoxal bis(guanylhydrazone) bis(guanylhydrazone), diethyglyoxal bis(guanylhydrazone), and 5'-deoxy-5'-{N-methyl-N-}aminoadenosine.

6. The process as claimed in claim 1 in which the amount of said inhibitor of 5-adenosylmethionine decarboxylase is from 1 to 5000 micrograms per square centimeter of skin.

7. The process as claimed in claim 2 in which the amount of said inhibitor of S-adenosylmethionine decarboxylase is from 1 to 5000 micrograms per square centimeter of skin and the amount of said inhibitor of ornithine decarboxylase is from 1 to 2000 micrograms per square centimeter of skin.

8. The process as claimed in claim 3 in which the amount of said inhibitor of S-adenosylmethionine decarboxylase is from 1 to 5000 micrograms per square centimeter of skin and the amount of said inhibitor of ornithine decarboxylase is from 1 to 2000 micrograms per square centimeter of skin.

9. The process as claimed in claim 4 in which the amount of said inhibitor of S-adenosylmethionine decarboxylase is from 1 to 5000 micrograms per square centimeter of skin and the amount of said inhibitor of ornithine decarboxylase is from 1 to 2000 micrograms per square centimeter of skin.

10. The process as claimed in claim 5 in which the amount of said inhibitor of S-adenosylmethionine decarboxylase is from 1 to 5000 micrograms per square centimeter of skin and the amount of said inhibitor of ornithine decarboxylase is from 1 to 2000 micrograms per square centimeter of skin.

* * * * *

UNITED STATES PATENT AND TRADEMARK OFFICE
CERTIFICATE OF CORRECTION

PATENT NO. : 5,132,293

DATED : July 21, 1992

INVENTOR(S) : Douglas Shander, F. Eugene Harrington, Gurpreet S. Ahluwalia

It is certified that error appears in the above-identified patent and that said Letters Patent is hereby corrected as shown below:

On the title page, item [56] References Cited, under Other Publications, "De Young et al.,... γ-Glutamyltranspeptidase..." should be --De Young et al.,... gamma-Glutamyltranspeptidase...--

Col. 2, line 4, delete ")" after "rate, ""
    Col. 3, line 29, insert --1-- before "to"
    Col. 3, line 36, change "1:0 to 10:1" to --1:10 to 10:1--
    Col. 4, line 60, "SAMDA" should be --SAMDC--
    Col. 5, line 11, "-ornithing" should be ---ornithine--
    Col. 5, line 18, delete "bis(guanylhydrazone), diethyglyoxal bis(guanyl-
    Col. 5, line 19, delete "hydrazone)"

Signed and Sealed this

Seventh Day of September, 1993

Attest:

BRUCE LEHMAN

Attesting Officer     Commissioner of Patents and Trademarks